(12) United States Patent
Coalter, III et al.

(10) Patent No.: US 11,945,896 B2
(45) Date of Patent: Apr. 2, 2024

(54) CATALYST COMPOSITION AND SYSTEM HAVING EXTENDED LIFETIME

(71) Applicant: W.R. Grace & Co.-CONN., Columbia, MD (US)

(72) Inventors: Joseph Coalter, III, Columbia, MD (US); Rose Kent, Columbia, MD (US); Adam Marwitz, Columbia, MD (US); Ronald Epstein, Columbia, MD (US); Michael Elder, Columbia, MD (US)

(73) Assignee: W.R. Grace & Co.-CONN., Columbia, MD (US)

( * ) Notice: Subject to any disclaimer, the term of this patent is extended or adjusted under 35 U.S.C. 154(b) by 0 days.

(21) Appl. No.: 17/761,451

(22) PCT Filed: Sep. 10, 2020

(86) PCT No.: PCT/US2020/050042
§ 371 (c)(1),
(2) Date: Mar. 17, 2022

(87) PCT Pub. No.: WO2021/055212
PCT Pub. Date: Mar. 25, 2021

(65) Prior Publication Data
US 2022/0380491 A1 Dec. 1, 2022

Related U.S. Application Data

(60) Provisional application No. 62/902,048, filed on Sep. 18, 2019.

(51) Int. Cl.
*C08F 110/06* (2006.01)
*C08F 4/646* (2006.01)
*C08F 4/654* (2006.01)

(52) U.S. Cl.
CPC .......... *C08F 4/6541* (2013.01); *C08F 4/6465* (2013.01); *C08F 110/06* (2013.01)

(58) Field of Classification Search
CPC ..................................................... C08F 110/06
See application file for complete search history.

(56) References Cited

U.S. PATENT DOCUMENTS

| | | | |
|---|---|---|---|
| 4,399,054 A * | 8/1983 | Ferraris | C08F 10/00 526/124.8 |
| 5,124,298 A | 6/1992 | Job | |
| 5,468,698 A | 11/1995 | Koskinen et al. | |
| 5,962,361 A | 10/1999 | Zum Mallen | |
| 6,818,711 B2 | 11/2004 | Bauch | |
| 2008/0207972 A1 | 8/2008 | Uhrhammer et al. | |
| 2010/0204506 A1 | 8/2010 | Chen et al. | |
| 2013/0261272 A1 | 10/2013 | Herzog et al. | |
| 2013/0261273 A1 * | 10/2013 | Chen | C08F 4/16 526/194 |
| 2014/0163184 A1 | 6/2014 | Chen et al. | |
| 2016/0090428 A1 * | 3/2016 | Mignogna | C07C 327/28 502/122 |
| 2018/0057621 A1 | 3/2018 | Mignogna et al. | |
| 2019/0194438 A1 | 7/2019 | Van Egmond | |
| 2019/0211118 A1 | 7/2019 | Elder et al. | |

FOREIGN PATENT DOCUMENTS

WO WO-2018067367 A1 * 4/2018 .............. C08F 10/06

OTHER PUBLICATIONS

International Search Report and Written Opinion issued in International Patent Application No. PCT/US2020/050042, dated Dec. 10, 2020.
European Extended Search Report, EP20864777.6, dated Sep. 27, 2023, 9 pages.

* cited by examiner

*Primary Examiner* — Catherine S Branch
(74) *Attorney, Agent, or Firm* — Foley & Lardner LLP

(57) ABSTRACT

A Ziegler-Natta catalyst composition is disclosed. The catalyst composition includes an internal electron donor with improved polymerization kinetics, a long lifetime, improved stereoselectivity and/or improved hydrogen response.

21 Claims, No Drawings

CATALYST COMPOSITION AND SYSTEM HAVING EXTENDED LIFETIME

RELATED APPLICATIONS

The present application is the U.S. National Stage of International Patent Application No. PCT/US2020/050042, filed Sep. 10, 2020, which claims priority from U.S. Patent Application No. 62/902,048, filed Sep. 18, 2019. The contents of these applications are incorporated herein by reference in their entirety.

BACKGROUND

Polyolefin polymers are used in numerous and diverse applications and fields. Polyolefin polymers, for instance, are thermoplastic polymers that can be easily processed. The polyolefin polymers can also be recycled and reused. Polyolefin polymers are formed from hydrocarbons, such as ethylene and alpha-olefins, which are obtained from petrochemicals and are abundantly available.

Polypropylene polymers, which are one type of polyolefin polymers, generally have a linear structure based on a propylene monomer. Polypropylene polymers can have various different stereospecific configurations. Polypropylene polymers, for example, can be isotactic, syndiotactic, and atactic. Isotactic polypropylene is perhaps the most common form and can be highly crystalline. Polypropylene polymers that can be produced include homopolymers, modified polypropylene polymers, and polypropylene copolymers which include polypropylene terpolymers. By modifying the polypropylene or copolymerizing the propylene with other monomers, various different polymers can be produced having desired properties for a particular application. For example, polypropylene copolymers can be produced having elastomeric properties which greatly enhances the impact strength of the polymers.

Worldwide demand for olefin-based polymers continues to grow as applications for these polymers become more diverse and more sophisticated. Known are Ziegler-Natta catalyst compositions for the production of olefin-based polymers. Ziegler-Natta catalyst compositions typically include a procatalyst containing a transition metal halide (i.e., titanium, chromium, vanadium), a cocatalyst such as an organoaluminum compound, and optionally an external electron donor.

Given the perennial emergence of new applications for olefin-based polymers, the art recognizes the need for olefin-based polymers with improved and
  varied properties. In addition, a need exists for improved Ziegler-Natta catalyst compositions that offer one or more benefits for further improving polymer production processes and/or polymer properties. In particular, a need exists for improved Ziegler-Natta catalyst compositions that have improved polymerization kinetics especially in regard to initial activity and/or prepoly activity, a longer catalyst lifetime while maintaining excellent stereoselectivity, hydrogen response, and activity.

SUMMARY

In general, the present disclosure is directed to a catalyst system for producing polyolefin polymers. The catalyst system includes a catalyst composition containing an internal electron donor. The internal electron donor provides the catalyst composition with a relatively long lifetime and provides the catalyst composition with a more uniform polymerization kinetics profile. The catalyst system of the present disclosure is capable of producing polyolefin polymers having different and desired properties.

For example, in one embodiment, the present disclosure is directed to a catalyst composition for stereoselective polymerization of an olefin, such as propylene. The catalyst composition includes a combination of a magnesium moiety, a titanium moiety, and an internal electron donor. The internal electron donor has the following chemical structure:

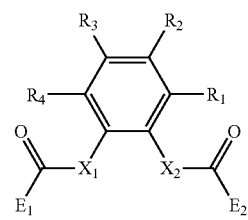

wherein RD and $R_4$ are each a saturated or unsaturated hydrocarbyl group having from 1 to 20 carbon atoms, and wherein at least one of $R_2$ and $R_3$ is hydrogen, and wherein at least one of $R_2$ and $R_3$ comprises a substituted or unsubstituted hydrocarbyl group having from 5 to 15 carbon atoms, the hydrocarbyl group having a branched or linear structure or comprising a cycloalkyl 2 group having from 7 to 15 carbon atoms, such as from 7 to 15 carbon atoms, and where $E_1$ and $E_2$ are the same or different and selected from the group consisting of an alkyl having 1 to 20 carbon atoms, a substituted alkyl having 1 to 20 carbon atoms, an aryl having 6 to 20 carbon atoms, a substituted aryl having 6 to 20 carbon atoms, or an inert functional group having 1 to 20 carbon atoms and optionally containing heteroatoms, and wherein $X_1$ and $X_2$ are each O, S, an alkyl group or $NR_5$ and wherein $R_5$ is a hydrocarbyl group having 1 to 20 carbon atoms or is hydrogen.

In one embodiment, at least one of $R_2$ and $R_3$ of the internal electron donor comprises a branched alkyl or alkenyl group. The branched alkyl or alkenyl group can contain, for instance, from about 5 to about 10 carbon atoms. In one embodiment, at least one of $R_2$ and $R_3$ of the internal electron donor comprises a 3-pentyl group, a 2-pentyl group, a cycloheptyl group, or a cyclooctyl group.

$R_1$ and $R_4$ of the internal electron donor can be the same or different. In one embodiment, both $R_1$ and $R_4$ are linear hydrocarbyl groups. The hydrocarbyl groups, for instance, may have from about 1 to about 8 carbon atoms. For instance, $R_1$ and $R_4$ may comprise a C1 to C8 alkyl group, a C2 to C8 alkenyl group, or mixtures thereof. In one embodiment, $R_1$ and $R_4$ are the same and both comprise an alkyl group, such as a methyl or ethyl group.

In one embodiment, the internal electron donor is a non-phthalate, substituted phenylene aromatic diester. For instance, E1 and E2 may both comprise phenyl groups.

The catalyst composition of the present disclosure can contain various other components, for instance the catalyst composition may include a cocatalyst. The cocatalyst may comprise a hydrocarbon aluminum compound, such as triethylaluminum. The composition may also contain a selectivity control agent. The selectivity control agent may comprise an alkoxy silane. For example, the selectivity control agent may comprise dicyclopentyldimethoxysilane, di-tert-butyldimethoxysilane, methylcyclohexyldimethoxysilane, methylcyclohexyldiethoxysilane, ethylcyclohexyldimethoxysilane, diphenyldimethoxysilane, diisopropyldimethoxysilane, di-n-propyldimethoxysilane, diisobutyldimethoxysilane, diisobutyldiethoxysilane, isobutylisopropyldimethoxysilane, di-n-butyldimethoxysilane, cyclopentyltrimethoxysilane, isopropyltrimethoxysilane, n-propyltrimethoxysilane, n-propyltriethoxysilane, ethyltriethoxysilane, tetramethoxysilane, tetraethoxysilane, diethylaminotriethoxysilane, cyclopentylpyrrolidinodimethoxysilane, bis(pyrrolidino)dimethoxysilane, bis(perhydroisoquinolino)dimethoxysilane, dimethyldimethoxysilane or mixtures thereof.

In still another embodiment, the catalyst composition may include an activity limiting agent. In one embodiment, the composition may contain a mixed external electron donor.

In addition to being directed to a catalyst composition, the present disclosure is also directed to a polymerization process for producing an olefin polymer. The process includes polymerizing an olefin in the presence of the catalyst composition as described above. In one embodiment, the olefin may comprise a combination of propylene and ethylene for forming a propylene and ethylene copolymer. In one particular embodiment, for instance, the process produces a heterophasic polymer. The heterophasic polymer may comprise a first polymer phase comprising a polypropylene homopolymer or a polypropylene random copolymer combined with a second polymer phase that comprises an elastomeric propylene ethylene copolymer.

The present disclosure is also directed to an olefin polymer produced using the catalyst composition as described above.

Other features and aspects of the present disclosure are discussed in greater detail below.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to catalyst systems for producing polyolefin polymers, particularly polypropylene polymers. The present disclosure is also directed to a catalyst composition and to methods of polymerizing and copolymerizing olefins using the catalyst composition. In general, the catalyst composition of the present disclosure includes a magnesium moiety, a titanium moiety, and an internal electron donor. The internal electron donor includes a unique combination of substituted groups that has been found to significantly improve the performance of the catalyst composition.

More particularly, the internal electron donor of the present disclosure is a phenylene substituted compound that includes a relatively large ring or branched alkyl/alkylene. The internal electron donor, for instance, is believed to provide the catalyst composition with a surprisingly longer lifetime, meaning that the catalyst displays catalytic activity within a reactor for an extended period of time, especially in relation to previous catalysts. Although unknown, it is believed that certain substitution patterns and functional groups provide a lower activity during catalyst initiation and a flatter polymerization kinetic profile that remains uniform for an extended period of time, instead of kinetic profile featuring high initiation activity and rapid catalyst activity decay. In this manner, polymerization processes can be carried out according to the present disclosure with better controls and longer reaction times in order to form polymers with unique properties.

In addition to the above, the catalyst composition of the present disclosure can also offer various other benefits and advantages. The catalyst composition for instance, in some embodiments, can provide improved prepoly kinetics. For example, catalyst compositions made according to the present disclosure display more stable kinetics that do not result in catalyst overheating during pre-polymerization or during the initial phase of polymerization. Overheating, for instance, can cause catalyst degradation and reduction in efficiency as well as issues with morphology. The catalyst systems of the present disclosure, however, display a more uniform kinetic profile that results in increased polymerization efficiency over extended times.

In addition, in some processes, the catalyst composition can provide improved stereoselectivity and/or higher hydrogen response compared to previous non-phthalate catalysts. In one embodiment, for instance, the catalyst composition can provide a similar kinetic profile to a phthalate-based catalyst without having to incorporate a phthalate-based compound into the process.

As used herein, an internal electron donor is a compound added during formation of the catalyst composition that donates electrons to one or more metals present in the resultant composition. It is believed that the internal electron donor assists in regulating the formation of active sites and thus enhances catalyst stereoselectivity. In one embodiment, the internal electron donor of the present disclosure has the following chemical formula:

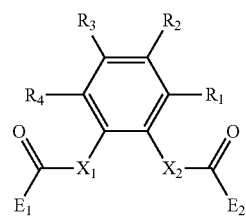

Formula I wherein $R_1$ and $R_4$ are each a saturated or unsaturated hydrocarbyl group having from 1 to 20 carbon atoms, and wherein at least one of $R_2$ and $R_3$ is hydrogen, and wherein at least one of $R_2$ and $R_3$ comprises a substituted or unsubstituted hydrocarbyl group having from 5 to 15 carbon atoms, the hydrocarbyl group having a branched or linear structure or comprising a cycloalkyl group having from 5 to 15 carbon atoms, such as from 7 to 15 carbon atoms, aryl and substituted aryl groups, and where $E_1$ and $E_2$ are the same or different and selected from the group consisting of an alkyl having 1 to 20 carbon atoms, a substituted alkyl having 1 to 20 carbon atoms, an aryl having 6 to 20 carbon atoms, a substituted aryl having 6 to 20 carbon atoms, or an inert functional group having 1 to 20 carbon atoms and optionally containing heteroatoms, and wherein $X_1$ and $X_2$ are each O, S, an alkyl group or $NR_5$ and wherein $R_5$ is a hydrocarbyl group having 1 to 20 carbon atoms or is hydrogen.

As used herein, the term "hydrocarbyl" and "hydrocarbon" refer to substituents containing only hydrogen and carbon atoms, including branched or unbranched, saturated or unsaturated, cyclic, polycyclic, fused, or acyclic species, and combinations thereof. Nonlimiting examples of hydrocarbyl groups include alkyl-, cycloalkyl-, alkenyl-, alkadienyl-, cycloalkenyl-, cycloalkadienyl-, aryl-, aralkyl, alkylaryl, and alkynyl- groups.

As used herein, the terms "substituted hydrocarbyl" and "substituted hydrocarbon" refer to a hydrocarbyl group that is substituted with one or more 6 nonhydrocarbyl substituent groups. A nonlimiting example of a nonhydrocarbyl substituent group is a heteroatom. As used herein, a "heteroatom" refers to an atom other than carbon or hydrogen. The heteroatom can be a non-carbon atom from Groups 13, 14, 15, 16 or 17 of the Periodic TableNonlimiting examples of heteroatoms include: halogens (F, Cl, Br, I), N, O, P, B, S, and Si. A substituted hydrocarbyl group also includes a halohydrocarbyl group and a silicon-containing hydrocarbyl group. As used herein, the term "halohydrocarbyl" group refers to a hydrocarbyl group that is substituted with one or more halogen atoms. As used herein, the term "silicon-containing hydrocarbyl group" is a hydrocarbyl group that is substituted with one or more silicon atoms. The silicon atom(s) may or may not be in the carbon chain.

In one embodiment, the above internal electron donor can be combined with a magnesium moiety and a titanium moiety in producing the catalyst composition.

The internal electron donor as shown above with respect to Formula I includes R1 through R4 groups that provide many of the benefits associated with the catalyst composition of the present disclosure. In one embodiment, R1 and R4 are identical or very similar. In one embodiment, for instance, R1 and R4 are linear hydrocarbyl groups. For instance, R1 and R4 may comprise a C1 to C8 alkyl group, a C2 to C8 alkenyl group, or mixtures thereof. For example, in one embodiment, R1 and R4 may both comprise alkyl groups that have the same carbon chain length or vary in carbon chain length by no more than about 3 carbons atoms, such as by no more than about 2 carbon atoms.

In one embodiment, R4 is a methyl group, while R1 is a methyl group, an ethyl group, a propyl group, or a butyl group, or vice versa. In another alternative embodiment, both R1 and R4 are methyl groups, both R1 and R4 are ethyl groups, both R1 and R4 are propyl groups, or both R1 and R4 are butyl groups.

In conjunction with the above described R1 and R4 groups, at least one of R2 or R3 is a substituted group that is larger or bulkier than the R1 and R4 groups. The other of R2 or R3 can be hydrogen. The larger or bulky group situated at R2 or R3, for instance, can be a hydrocarbyl group having a branched or linear structure or may comprise a cycloalkyl group having from 7 to 15 carbon atoms. The cycloalkyl group, for instance, may be a cycloheptyl group or a cyclooctyl group. When either R2 or R3 has a branched or linear structure, on the other hand, R2 or R3 may be a pentyl group, a heptyl group, an octyl group, a nonyl group, a decyl group, or the like. For instance, R2 or R3 may be a 3-pentyl group or a 2-pentyl group.

Further examples of internal electron donors made in accordance with the present disclosure are shown below. In each of the below structures, R1 through R4 can be substituted with any of the groups in any of the combinations described above.

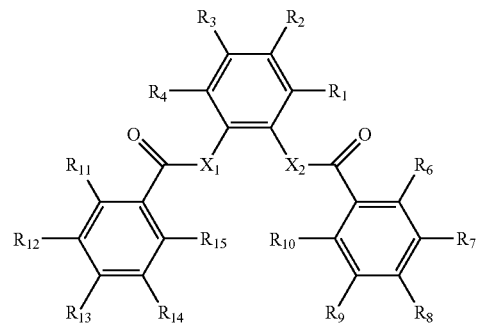

Formula II wherein R6 through R15 can be the same or different. Each of R6 through R15 is selected from a hydrogen, substituted hydrocarbyl groups having 1 to 20 carbon atoms, and unsubstituted hydrocarbyl groups having 1 to 20 carbon atoms, an alkoxyl group having 1 to 20 carbon atoms, a hetero atom, and combinations thereof.

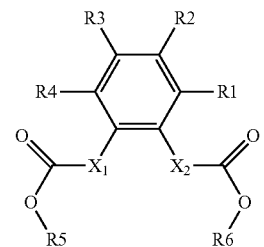

Formula III wherein X1 and X2 above can be oxygen, sulfur or a nitrogen containing group. In one embodiment, for instance, X1 is oxygen and X2 is sulfur. R5 and R6 can comprise independent alkyl groups or aryl groups. R5 and R6, for example, can comprise $C_1$ to $C_8$ alkyl groups.

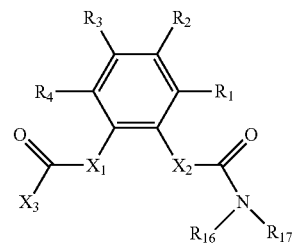

Formula IV wherein R16 and R17 are independently hydrogen or a C1 to C20 hydrocarbyl group. In the above formula, X1 and X2 can be oxygen, sulfur, or a nitrogen group. Alternatively, one or both of X1 and X2 maybe a hydrocarbyl group, such as an alkyl group containing 1 to 3 carbon atoms. X3 is a —OR group or a —NR1R2 group in which R, R1 or R2 are selected from a C1 to C20 hydrocarbyl group optionally containing a heteroatom selected from a halogen, phosphorous, sulfur, nitrogen, or oxygen. In one embodiment, $X_1$ is a carbon atom and $X_3$ is an ethyl group.

Formula V
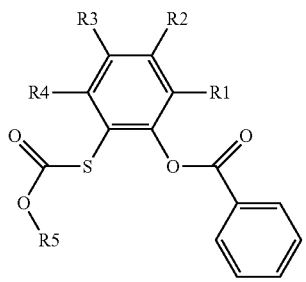
wherein $R_5$ can be an alkyl group or an aryl group. For example, $R_5$ can be a $C_1$ to $C_8$ alkyl group.
Formula VI
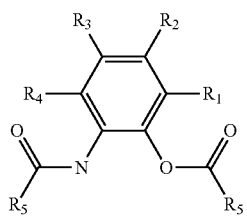
Formula VII
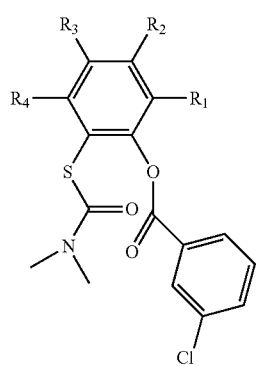
Formula VIII
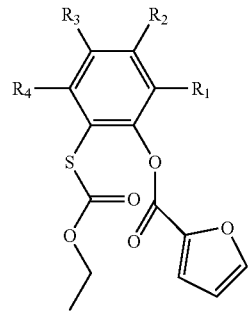
Formula IX
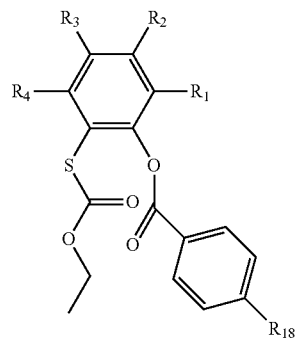
wherein R18 is hydrogen or a hydrocarbyl group containing from about 1 to about 8 carbon atoms.
Formula X
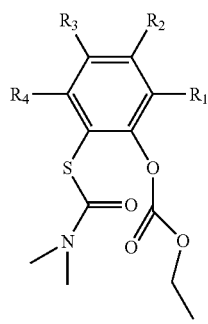
Formula XI
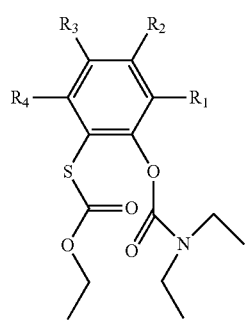
Formula XII
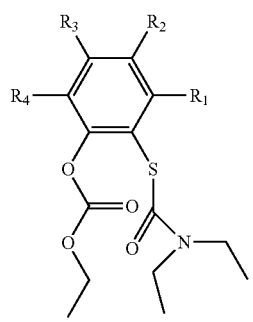

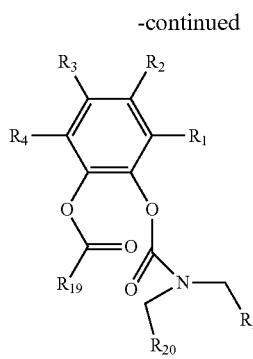

Formula XIII wherein R19, R20 and R21 are the same or different and may be selected from a hydrocarbyl group having from about 1 to about 15 carbon atoms optionally containing a heteroatom selected from a halogen, phosphorous, sulfur, nitrogen, or oxygen. R20 and R21 can be the same or different and can be fused together to form 1 or more cyclic groups.

The internal electron donor made in accordance with the present disclosure is combined with a catalyst precursor. The catalyst precursor can include (i) magnesium, (ii) a transition metal compound of an element from Periodic Table groups 4 to 8, (iii) a halide, an oxyhalide, and/or an alkoxide of (i) and/or (ii), and (iv) combinations of (i), (ii), and (iii). Nonlimiting examples of suitable catalyst precursors include halides, oxyhalides, and alkoxides of magnesium, manganese, titanium, vanadium, chromium, molybdenum, zirconium, hafnium, and combinations thereof.

In an embodiment, the preparation of the catalyst precursor involves halogenation of mixed magnesium and titanium alkoxides.

In an embodiment, the catalyst precursor is a magnesium moiety compound (MagMo), a mixed magnesium titanium compound (MagTi), or a benzoate-containing magnesium chloride compound (BenMag). In an embodiment, the catalyst precursor is a magnesium moiety ("MagMo") precursor. The MagMo precursor includes a magnesium moiety. Nonlimiting examples of suitable magnesium moieties include anhydrous magnesium chloride and/or its alcohol adduct, magnesium alkoxide or aryloxide, mixed magnesium alkoxy halide, and/or carboxylated magnesium dialkoxide or aryloxide. In one embodiment, the MagMo precursor is a magnesium di($C_{1-4}$)alkoxide. In a further embodiment, the MagMo precursor is diethoxymagnesium.

In an embodiment, the catalyst precursor is a mixed magnesium/titanium compound ("MagTi"). The "MagTi precursor" has the formula $Mg_dTi(OR^e)_fX_g$ wherein $R^e$ is an aliphatic or aromatic hydrocarbon radical having 1 to 14 carbon atoms or COR' wherein R' is an aliphatic or aromatic hydrocarbon radical having 1 to 14 carbon atoms; each $OR^e$ group is the same or different; X is independently chlorine, bromine or iodine, preferably chlorine; d is 0.5 to 56, or 2 to 4; f is 2 to 116 or 5 to 15; and g is 0.5 to 116, or 1 to 3. The precursors are prepared by controlled precipitation through removal of an alcohol from the reaction mixture used in their preparation. In an embodiment, a reaction medium comprises a mixture of an aromatic liquid, especially a chlorinated aromatic compound, most especially chlorobenzene, with an alkanol, especially ethanol. Suitable halogenating agents include titanium tetrabromide, titanium tetrachloride or titanium trichloride, especially titanium tetrachloride. Removal of the alkanol from the solution used in the halogenation, results in precipitation of the solid precursor, having especially desirable morphology and surface area. Moreover, the resulting precursors are particularly uniform in particle size.

In an embodiment, the catalyst precursor is a benzoate-containing magnesium chloride material ("BenMag"). As used herein, a "benzoate-containing magnesium chloride" ("BenMag") can be a catalyst (i.e., a halogenated catalyst precursor) containing a benzoate internal electron donor. The BenMag material may also include a titanium moiety, such as a titanium halide. The benzoate internal donor is labile and can be replaced by other electron donors during catalyst and/or catalyst synthesis. Nonlimiting examples of suitable benzoate groups include ethyl benzoate, methyl benzoate, ethyl p-methoxybenzoate, methyl p-ethoxybenzoate, ethyl p-ethoxybenzoate, ethyl p-chlorobenzoate. In one embodiment, the benzoate group is ethyl benzoate. In an embodiment, the BenMag catalyst precursor may be a product of halogenation of any catalyst precursor (i.e., a MagMo precursor or a MagTi precursor) in the presence of a benzoate compound.

In one embodiment, a substantially spherical $MgCl_2$-nEtOH adduct may be formed by a spray crystallization process. In the process, a $MgCl_2$-nROH melt, where n is 1-6, is sprayed inside a vessel while conducting inert gas at a temperature of 20-80° C. into the upper part of the vessel. The melt droplets are transferred to a crystallization area into which inert gas is introduced at a temperature of −50 to 20° C. crystallizing the melt droplets into nonagglomerated, solid particles of spherical shape. The spherical $MgCl_2$ particles are then classified into the desired size. Particles of undesired size can be recycled. In preferred embodiments for catalyst synthesis the spherical $MgCl_2$ precursor has an average particle size (Malvern $d_{50}$) of between about 15-150 microns, preferably between 20-100 microns, and most preferably between 35-85 microns.

The above spherical procatalyst precursor is referred to as a "spray crystallized" catalyst precursor. In one embodiment, the spray crystallized precursor can be dealcoholated. For instance, the spray crystallized treatment can undergo a post-treatment process in order to remove ethanol. For example, the ethanol/magnesium chloride weight ratio can be less than about 3.5:1, such as from about 3:1 to about 1.75:1, such as from about 2:1 to about 2.5:1.

In an embodiment, the catalyst precursor is converted to a solid catalyst by way of halogenation. Halogenation includes contacting the catalyst precursor with a halogenating agent in the presence of the internal electron donor. Halogenation converts the magnesium moiety present in the catalyst precursor into a magnesium halide support upon which the titanium moiety (such as a titanium halide) is deposited. Not wishing to be bound by any particular theory, it is believed that during halogenation the internal electron donor (1) regulates the position of titanium on the magnesium-based support, (2) facilitates conversion of the magnesium and titanium moieties into respective halides and (3) regulates the crystallite size of the magnesium halide support during conversion. Thus, provision of the internal electron donor yields a catalyst composition with enhanced stereoselectivity.

In an embodiment, the halogenating agent is a titanium halide having the formula $Ti(OR^e)_fX_h$ wherein $R^e$ and X are defined as above, f is an integer from 0 to 3; h is an integer from 1 to 4; and f+h is 4. In an embodiment, the halogenating agent is $TiCl_4$. In a further embodiment, the halogenation is conducted in the presence of a chlorinated or a non-chlorinated aromatic liquid, such as dichlorobenzene, o-chlorotoluene, chlorobenzene, benzene, toluene, a xylene or mixtures thereof.

In an embodiment, the reaction mixture is heated during halogenation. The catalyst precursor and halogenating agent are contacted initially at a temperature of less than about 10° C., such as less than about 0° C., such as less than about −10° C., such as less than about −20° C., such as less than about −30° C. The initial temperature is generally greater than about −50° C., such as greater than about −40° C. The mixture is then heated at a rate of 0.1 to 10.0° C./minute, or at a rate of 1.0 to 5.0° C./minute. The internal electron donor may be added later, after an initial contact period between the halogenating agent and catalyst precursor. Temperatures for the halogenation are from −40° C. to 150° C. (or any value or subrange therebetween), or from 0° C. to 120° C. Halogenation may be continued in the substantial absence of the internal electron donor for a period from 5 to 120 minutes, or from 10 to 50 minutes.

The manner in which the catalyst precursor, the halogenating agent and the internal electron donor are contacted may be varied. In an embodiment, the catalyst precursor is first contacted with a mixture containing the halogenating agent and a chlorinated aromatic compound. The resulting mixture is stirred and may be heated if desired. Next, the internal electron donor is added to the same reaction mixture without isolating or recovering of the precursor. The foregoing process may be conducted in a single reactor with addition of the various ingredients controlled by automated process controls.

In an embodiment, the catalyst precursor is contacted with the internal electron donor before reacting with the halogenating agent.

Contact times of the catalyst precursor with the internal electron donor are at least 10 minutes, or at least 15 minutes, or at least 20 minutes, or at least 1 hour at a temperature from at least −30° C., or at least −20° C., or at least 10° C. up to a temperature of 150° C., or up to 120° C., or up to 115° C., or up to 110° C.

In an embodiment, the catalyst precursor, the internal electron donor, and the halogenating agent are added simultaneously or substantially simultaneously.

The halogenation procedure may be repeated one, two, three, or more times as desired. In an embodiment, the resulting solid material is recovered from the reaction mixture and contacted one or more times in the absence (or in the presence) of the same (or different) internal electron donor components with a mixture of the halogenating agent in the chlorinated aromatic compound for at least about 10 minutes, or at least about 15 minutes, or at least about 20 minutes, and up to about 10 hours, or up to about 45 minutes, or up to about 30 minutes, at a temperature from at least about −20° C., or at least about 0° C., or at least about 10° C., to a temperature up to about 150° C., or up to about 120° C., or up to about 115° C.

After the foregoing halogenation procedure, the resulting solid catalyst composition is separated from the reaction medium employed in the final process, by filtering for example, to produce a moist filter cake. The moist filter cake may then be rinsed or washed with a liquid diluent to remove unreacted $TiCl_4$ and may be dried to remove residual liquid, if desired. Typically the resultant solid catalyst composition is washed one or more times with a "wash liquid," which is a liquid hydrocarbon such as an aliphatic hydrocarbon such as isopentane, isooctane, isohexane, hexane, pentane, or octane. The solid catalyst composition then can be separated and dried or slurried in a hydrocarbon, especially a relatively heavy hydrocarbon such as mineral oil for further storage or use.

In an embodiment, the resulting solid catalyst composition has a titanium content of from about 1.0 percent by weight to about 6.0 percent by weight, based on the total solids weight, or from about 1.5 percent by weight to about 4.5 percent by weight, or from about 2.0 percent by weight to about 3.5 percent by weight. The weight ratio of titanium to magnesium in the solid catalyst composition is suitably between about 1:3 and about 1:160, or between about 1:4 and about 1:50, or between about 1:6 and 1:30. In an embodiment, the internal electron donor may be present in the catalyst composition in a molar ratio of internal electron donor to magnesium of from about 0.005:1 to about 1:1, or from about 0.01:1 to about 0.4:1. Weight percent is based on the total weight of the catalyst composition.

In an embodiment, the catalyst composition may be further treated by one or more of the following procedures prior to or after isolation of the solid catalyst composition. The solid catalyst composition may be contacted (halogenated) with a further quantity of titanium halide compound.

Not wishing to be bound by any particular theory, it is believed that (1) further halogenation by contacting the previously formed catalyst composition with a titanium halide compound, especially a solution thereof in a halohydrocarbon diluent, and/or (2) further washing the previously formed catalyst composition with a halohydrocarbon at an elevated temperature (100-150° C.), results in desirable modification of the catalyst composition, possibly by removal of certain inactive or undesired metal compounds that are soluble in the foregoing diluent. Accordingly, in an embodiment, the catalyst is contacted with a halogenating agent, such as a mixture of a titanium halide and a halohydrocarbon diluent, such as $TiCl_4$ and chlorobenzene, one or more times prior to isolation or recovery. In another embodiment, the catalyst is washed at a temperature between 100 to 150° C. with chlorobenzene or o-chlorotoluene one or more times prior to isolation or recovery.

The present process for producing a catalyst composition may comprise two or more embodiments disclosed herein.

As described above, the catalyst composition can include a combination of a magnesium moiety, a titanium moiety and the internal electron donor. The catalyst composition is produced by way of the foregoing halogenation procedure which converts the catalyst precursor and the internal electron donor into the combination of the magnesium and titanium moieties, into which the internal electron donor is incorporated. The catalyst precursor from which the catalyst composition is formed can be the magnesium moiety precursor, the mixed magnesium/titanium precursor, the benzoate-containing magnesium chloride precursor or the spherical precursor.

In an embodiment, the magnesium moiety is a magnesium halide. In another embodiment, the magnesium halide is magnesium chloride, or magnesium chloride alcohol adduct.

In an embodiment, the titanium moiety is a titanium halide such as a titanium chloride. In another embodiment the titanium moiety is titanium tetrachloride.

In another embodiment, the catalyst composition includes a magnesium chloride support upon which a titanium chloride is deposited and upon which the internal electron donor is incorporated.

The present disclosure is also directed to a catalyst system that includes the catalyst composition as described above combined with various other catalyst components. For example, in one embodiment, the catalyst composition includes a cocatalyst. As used herein, a "cocatalyst" is a substance capable of converting the procatalyst to an active polymerization catalyst. The cocatalyst may include halides such as chlorides, alkyls, or aryls of aluminum, lithium, zinc, tin, cadmium, beryllium, magnesium, and combinations thereof. In an embodiment, the cocatalyst is a hydrocarbyl aluminum cocatalyst represented by the formula $R_3Al$ wherein each R is an alkyl, cycloalkyl, aryl, or hydride radical; at least one R is a hydrocarbyl radical; two or three R radicals can be joined in a cyclic radical forming a heterocyclic structure; each R can be the same or different; and each R, which is a hydrocarbyl radical, has 1 to 20 carbon atoms, and preferably 1 to 10 carbon atoms. In a further embodiment, each alkyl radical can be straight or branched chain and such hydrocarbyl radical can be a mixed radical, i.e., the radical can contain alkyl, aryl, and/or cycloalkyl groups. Nonlimiting examples of suitable radicals are: methyl, ethyl, n-propyl, isopropyl, n-butyl, isobutyl, tert-butyl, n-pentyl, neopentyl, n-hexyl, 2-methylpentyl, n-heptyl, n-octyl, isooctyl, 2-ethylhexyl, 5,5-dimethylhexyl, n-nonyl, n-decyl, isodecyl, n-undecyl, n-dodecyl.

Nonlimiting examples of suitable hydrocarbyl aluminum compounds are as follows: triisobutylaluminum, tri-n-hexylaluminum, diisobutylaluminum chloride, di-n-hexylaluminum chloride, isobutylaluminum dichloride, n-hexylaluminum dichloride, diisobutylhexylaluminum, isobutyldihexylaluminum, trimethylaluminum, triethylaluminum, tri-n-propylaluminum, triisopropylaluminum, tri-n-butylaluminum, tri-n-octylaluminum, tri-n-decylaluminum, tri-n-dodecylaluminum. In an embodiment, the cocatalyst is selected from triethylaluminum, triisobutylaluminum, tri-n-hexylaluminum, diisobutylaluminum chloride, and di-n-hexylaluminum chloride.

In an embodiment, the cocatalyst is a hydrocarbyl aluminum compound represented by the formula $R_nAlX_{3-n}$ wherein n=1 or 2, R is an alkyl, and X is a halide or alkoxide.

In an embodiment, the cocatalyst is triethylaluminum. The molar ratio of aluminum to titanium is from about 5:1 to about 1000:1, or from about 10:1 to about 200:1, or from about 15:1 to about 150:1, or from about 20:1 to about 100:1. In another embodiment, the molar ratio of aluminum to titanium is about 45:1.

In an embodiment, the catalyst composition includes a selectivity control agent. As used herein, a "selectivity control agent" is a compound added independent of procatalyst formation and contains at least one functional group that is capable of donating electrons to a metal atom. Bounded by no particular theory, it is believed that the selectivity control agent enhances catalyst stereoselectivity, (i.e., to reduces xylene soluble material in the formant polymer).

In an embodiment, the selectivity control agent donor may be selected from one or more of the following: an alkoxysilane, an amine, an ether, a carboxylate, a ketone, an amide, a carbamate, a phosphine, a phosphate, a phosphite, a sulfonate, a sulfone, and/or a sulfoxide.

In an embodiment, the selectivity control agent donor is an alkoxysilane. The alkoxysilane has the general formula: $SiR_m(OR')_{4-m}$ (I) where R independently each occurrence is hydrogen or a hydrocarbyl or an amino group optionally substituted with one or more substituents containing one or more Group 14, 15, 16, or 17 heteroatoms, said R containing up to 20 atoms not counting hydrogen and halogen; R' is a $C_{1-4}$ alkyl group; and m is 0, 1, 2 or 3. In an embodiment, R is $C_{6-12}$ aryl, alkyl or aralkyl, $C_{3-12}$ cycloalkyl, $C_{3-12}$ branched alkyl, or $C_{3-12}$ cyclic or acyclic amino group, R' is $C_{1-4}$ alkyl, and m is 1 or 2. Nonlimiting examples of suitable silane compositions include dicyclopentyldimethoxysilane, di-tert-butyldimethoxysilane, methylcyclohexyldimethoxysilane, methylcyclohexyldiethoxysilane, ethylcyclohexyldimethoxysilane, diphenyldimethoxysilane, diisopropyldimethoxysilane, di-n-propyldimethoxysilane, diisobutyldimethoxysilane, diisobutyldiethoxysilane, isobutylisopropyldimethoxysilane, di-n-butyldimethoxysilane, cyclopentyltrimethoxysilane, isopropyltrimethoxysilane, n-propyltrimethoxysilane, n-propyltriethoxysilane, ethyltriethoxysilane, tetramethoxysilane, tetraethoxysilane, diethylaminotriethoxysilane, cyclopentylpyrrolidinodimethoxysilane, bis(pyrrolidino)dimethoxysilane, bis(perhydroisoquinolino)dimethoxysilane, and dimethyldimethoxysilane. In an embodiment, the silane composition is dicyclopentyldimethoxysilane (DCPDMS), methylcyclohexyldimethoxysilane (MChDMS), or n-propyltrimethoxysilane (NPTMS), and any combination of thereof.

In an embodiment, the selectivity control agent can be a mixture of at least 2 alkoxysilanes. In a further embodiment, the mixture can be dicyclopentyldimethoxysilane and methylcyclohexyldimethoxysilane, dicyclopentyldimethoxysilane and tetraethoxysilane, or dicyclopentyldimethoxysilane and n-propyltriethoxysilane.

In an embodiment, the selectivity control agent is selected from one or more of the following: a benzoate, a succinate, and/or a diolester. In another embodiment, the selectivity control agent is a diether.

In an embodiment, the catalyst composition includes an activity limiting agent (ALA). As used herein, an "activity limiting agent" ("ALA") is a material that reduces catalyst activity at elevated temperature (i.e., temperature greater than about 85° C.). An ALA inhibits or otherwise prevents polymerization reactor upset and ensures continuity of the polymerization process. Typically, the activity of Ziegler-Natta catalysts increases as the reactor temperature rises. Ziegler-Natta catalysts also typically maintain high activity near the melting point temperature of the polymer produced. The heat generated by the exothermic polymerization reaction may cause polymer particles to form agglomerates and may ultimately lead to disruption of continuity for the polymer production process. The ALA reduces catalyst activity at elevated temperature, thereby preventing reactor upset, reducing (or preventing) particle agglomeration, and ensuring continuity of the polymerization process.

The activity limiting agent may be a carboxylic acid ester, a diether, a poly(alkene glycol), poly(alkene glycol)ester, a diol ester, and combinations thereof. The carboxylic acid ester can be an aliphatic or aromatic, mono- or poly-carboxylic acid ester. Nonlimiting examples of suitable monocarboxylic acid esters include ethyl and methyl benzoate, ethyl p-methoxybenzoate, methyl p-ethoxybenzoate, ethyl p-ethoxybenzoate, ethyl acrylate, methyl methacrylate, ethyl acetate, ethyl p-chlorobenzoate, hexyl p-aminobenzoate, isopropyl naphthenate, n-amyl toluate, ethyl cyclohexanoate, propyl pivalate and pentyl valerate.

The aliphatic carboxylic acid ester may be a $C_4$-$C_{30}$ aliphatic acid ester, may be a mono- or a poly-(two or more) ester, may be straight chain or branched, may be saturated or unsaturated, and any combination thereof. The $C_4$-$C_{30}$ aliphatic acid ester may also be substituted with one or more Group 14, 15 or 16 heteroatom containing substituents. Nonlimiting examples of suitable $C_4$-$C_{30}$ aliphatic acid esters include $C_{1-20}$ alkyl esters of aliphatic $C_{4-30}$ monocarboxylic acids, $C_{1-20}$ alkyl esters of aliphatic $C_{8-20}$ monocarboxylic acids, $C_{1-4}$ allyl mono- and diesters of aliphatic $C_{4-20}$ monocarboxylic acids and dicarboxylic acids, $C_{1-4}$ alkyl esters of aliphatic $C_{8-20}$ monocarboxylic acids and dicarboxylic acids, and $C_{4-20}$ mono- or polycarboxylate derivatives of 02-100 (poly)glycols or C2-loo (poly) glycol ethers. In a further embodiment, the $C_4$-$C_{30}$ aliphatic acid ester may be a laurate, a myristate, a palmitate, a stearate, an oleates, a sebacate, (poly) (alkylene glycol) mono- or diacetates, (poly)(alkylene glycol) mono- or di-myristates, (poly)(alkylene glycol) mono- or di-laurates, (poly)(alkylene glycol) mono- or di-oleates, glyceryl tri(acetate), glyceryl tri-ester of $C_{2-40}$ aliphatic carboxylic acids, and mixtures thereof. In a further embodiment, the $C_4$-$C_{30}$ aliphatic ester is isopropyl myristate or di-n-butyl sebacate.

In an embodiment, the activity limiting agent includes a diether. The diether can be a 1,3-diether compound represented by the following structure (XV):

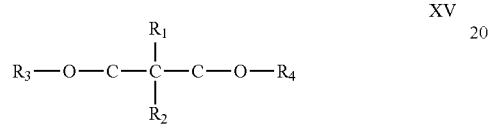

XV wherein $R_1$ to $R_4$ are independently of one another an alkyl, aryl or aralkyl group having up to 20 carbon atoms, which may optionally contain a group 14, 15, 16, or 17 heteroatom, and $R_1$ and $R_2$ may be a hydrogen atom. The dialkylether may linear or branched, and may include one or more of the following groups: alkyl, cycloaliphatic, aryl, alkylaryl or arylalkyl radicals with 1-18 carbon atoms, and hydrogen. $R_1$ and $R_2$ may be linked to form a cyclic structure, such as cyclopentadiene or fluorene.

In an embodiment, the activity limiting agent includes a succinate composition having the following structure (XVI):

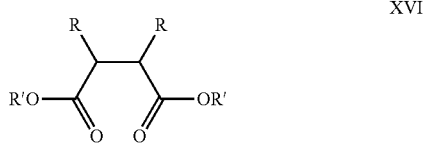

XVI wherein R and R' may be the same or different, R and/or R' including one or more of the following groups: hydrogen, linear or branched alkyl, alkenyl, cycloalkyl, aryl, arylalkyl or alkylaryl group, optionally containing heteroatoms. One or more ring structures can be formed via one or both 2- and 3-position carbon atom.

In an embodiment, the activity limiting agent includes a diol ester as represented by the following structure (XVII):

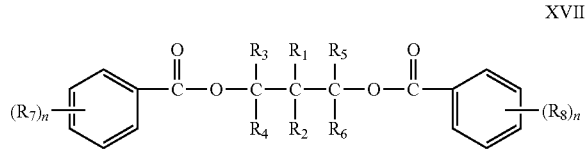

XVII wherein n is an integer from 1 to 5. $R_1$ and $R_2$, may be the same or different, and each may be selected from hydrogen, methyl, ethyl, n-propyl, i-propyl, n-butyl, i-butyl, t-butyl, allyl, phenyl, or halophenyl group. $R_3$, $R_4$, $R_5$, $R_6$, $R_7$, and $R_8$ may be the same or different, and each may be selected from hydrogen, halogen, substituted, or unsubstituted hydrocarbyl having 1 to 20 carbon atoms. $R_1$-$R_6$ groups may optionally contain one or more heteroatoms replacing carbon, hydrogen or both, the hetero-atom selected from nitrogen, oxygen, sulfur, silicon, phosphorus and a halogen. $R_7$ and $R_8$, may be the same or different, and may be bonded to any carbon atom of the 2-, 3-, 4-, 5-, and 6-position of either phenyl ring.

In one embodiment, the catalyst system includes a mixed external electron donor. A mixed external electron donor comprises at least two of the following components: (1) a first selectivity control agent, (2) a second selectivity control agent; and (3) an activity limiting agent.

In an embodiment, the selectivity control agent and/or activity limiting agent can be added into the reactor separately. In another embodiment, the selectivity control agent and the activity limiting agent can be mixed together in advance and then added into the reactor as a mixture. In the mixture, more than one selectivity control agent or more than one activity limiting agent can be used. In an embodiment, the mixture is dicyclopentyldimethoxysilane and isopropyl myristate, dicyclopentyldimethoxysilane and poly(ethylene glycol)laurate, dicyclopentyldimethoxysilane and isopropyl myristate and poly(ethylene glycol)dioleate, methylcyclohexyldimethoxysilane and isopropyl myristate, n-propyltrimethoxysilane and isopropyl myristate, dimethyldimethoxysilane and methylcyclohexyldimethoxysilane and isopropyl myristate, dicyclopentyldimethoxysilane and n-propyltriethoxysilane and isopropyl myristate, and dicyclopentyldimethoxysilane and tetraethoxysilane and isopropyl myristate, and combinations thereof.

In an embodiment, the catalyst composition includes any of the foregoing selectivity control agents in combination with any of the foregoing activity limiting agents.

The present catalyst composition may comprise two or more embodiments disclosed herein.

In an embodiment, a process for producing an olefin-based polymer is provided. The process includes contacting an olefin with a catalyst composition under polymerization conditions. The catalyst composition includes a substituted phenylene internal electron donor as described above. The process further includes forming an olefin-based polymer.

In an embodiment, the catalyst composition includes a catalyst composition and a cocatalyst. The catalyst composition may be any catalyst composition as disclosed herein. The catalyst composition may include a substituted phenylene compound as the internal electron donor. The cocatalyst may be any cocatalyst as disclosed herein. The catalyst composition may optionally include a selectivity control agent and/or an activity limiting agent as previously disclosed.

In an embodiment, the olefin-based polymer can be a propylene-based olefin, an ethylene-based olefin, and combinations thereof. In an embodiment, the olefin-based polymer is a propylene-based polymer.

One or more olefin monomers can be introduced into a polymerization reactor to react with the catalyst and to form a polymer, or a fluidized bed of polymer particles. Nonlimiting examples of suitable olefin monomers include ethylene, propylene, $C_{4-20}$ α-olefins, such as 1-butene, 1-pentene, 1-hexene, 4-methyl-1-pentene, 1-heptene, 1-octene, 1-decene, 1-dodecene and the like; $C_{4-20}$ diolefins, such as 1,3-butadiene, 1,3-pentadiene, norbornadiene, 5-ethylidene-2-norbornene (ENB) and dicyclopentadiene; $C_{8-40}$ vinyl aromatic compounds including styrene, o-, m-, and p-methylstyrene, divinylbenzene, vinylbiphenyl, vinylnapthalene; and halogen-substituted $C_{8-40}$ vinyl aromatic compounds such as chlorostyrene and fluorostyrene.

As used herein, "polymerization conditions" are temperature and pressure parameters within a polymerization reactor suitable for promoting polymerization between the catalyst composition and an olefin to form the desired polymer. The polymerization process may be a gas phase, a slurry, or a bulk polymerization process, operating in one, or more than one, reactor.

In an embodiment, polymerization occurs by way of gas phase polymerization. As used herein, "gas phase polymerization" is the passage of an ascending fluidizing medium, the fluidizing medium containing one or more monomers, in the presence of a catalyst through a fluidized bed of polymer particles maintained in a fluidized state by the fluidizing medium. "Fluidization," "fluidized," or "fluidizing" is a gas-solid contacting process in which a bed of finely divided polymer particles is lifted and agitated by a rising stream of gas. Fluidization occurs in a bed of particulates when an upward flow of fluid through the interstices of the bed of particles attains a pressure differential and frictional resistance increment exceeding particulate weight. Thus, a "fluidized bed" is a plurality of polymer particles suspended in a fluidized state by a stream of a fluidizing medium. A "fluidizing medium" is one or more olefin gases, optionally a carrier gas (such as $H_2$ or $N_2$) and optionally a liquid (such as a hydrocarbon) which ascends through the gas-phase reactor.

A typical gas-phase polymerization reactor (or gas phase reactor) includes a vessel (i.e., the reactor), the fluidized bed, a distribution plate, inlet and outlet piping, a compressor, a cycle gas cooler or heat exchanger, and a product discharge system. The vessel includes a reaction zone and a velocity reduction zone, each of which is located above the distribution plate. The bed is located in the reaction zone. In an embodiment, the fluidizing medium includes propylene gas and at least one other gas such as an olefin and/or a carrier gas such as hydrogen or nitrogen.

In addition to a gas-phase polymerization process, the catalyst composition of the present disclosure can also be used in a bulk-phase process. In a bulk polymerization process, the catalyst composition is contacted with one or more liquid monomers, such as liquid propylene. Hydrogen can also be contained within the reaction medium for controlling molecular weight of the resulting polymer.

In an embodiment, the contacting occurs by way of feeding the catalyst composition into a polymerization reactor and introducing the olefin into the polymerization reactor. In an embodiment, the cocatalyst can be mixed with the catalyst composition (pre-mix) prior to the introduction of the catalyst composition into the polymerization reactor. In another embodiment, the cocatalyst is added to the polymerization reactor independently of the catalyst composition. The independent introduction of the cocatalyst into the polymerization reactor can occur simultaneously, or substantially simultaneously, with the catalyst composition feed.

In an embodiment, the polymerization process may include a pre-polymerization step. Pre-polymerization includes adding the catalyst composition, after contacted with the co-catalyst and the selectivity control agent and/or the activity limiting agent, in an olefin polymerization step that results in a low degree of conversion of about 0.5 to about 1000 grams of polymer per gram of solid catalyst component. The pre-polymerization step can be conducted as part of a continuous polymerization process or separately in a batch process. When conducted as part of a continuous process the conversion of the pre-polymerized catalyst component is preferably from about 50 to about 500 g polymer per gram of solid catalyst component. The pre-polymerized catalyst stream is then introduced into the main polymerization reaction zone and contacted with the remainder of the olefin monomer to be polymerized, and optionally additional quantities of one or more of the cocatalyst and selectivity control agent components. Pre-polymerization results in the procatalyst composition being combined with the cocatalyst and the selectivity control agent and/or the activity limiting agent, the combination being dispersed in a matrix of the formant polymer. Optionally, additional quantities of the cocatalyst, the selectivity control agent and/or the activity limiting agent may be added.

In an embodiment, the polymerization process may include a pre-activation step. Pre-activation includes contacting the catalyst composition with the co-catalyst and the selectivity control agent and/or the activity limiting agent. The resulting preactivated catalyst stream is subsequently introduced into the polymerization reaction zone and contacted with the olefin monomer to be polymerized, and optionally one or more of the selectivity control agent components. Pre-activation results in the procatalyst composition being combined with the cocatalyst and the selectivity control agent and/or the activity limiting agent. Optionally, additional quantities of the selectivity control agent and/or the activity limiting agent may be added.

In an embodiment, the process includes mixing the selectivity control agent (and optionally the activity limiting agent) with the catalyst composition. The selectivity control agent can be complexed with the cocatalyst and mixed with the catalyst composition (pre-mix) prior to contact between the catalyst composition and the olefin. In another embodiment, the selectivity control agent and/or the activity limiting agent can be added independently to the polymerization reactor. In an embodiment, the selectivity control agent is dicyclopentyldimethoxysilane or n-propyltrimethoxysilane.

In another embodiment, the catalyst composition includes dicyclopentyldimethoxysilane or n-propyltrimethoxysilane and an activity limiting agent such as isopropyl myristate.

In an embodiment, a polypropylene homopolymer is produced in a first reactor. The content of the first reactor is subsequently transferred to a second reactor into which ethylene is introduced. This results in production of a propylene-ethylene copolymer in the second reactor.

In an embodiment, a polypropylene homopolymer is formed via introduction of propylene and any of the present catalyst compositions, cocatalysts, selectivity control agents, and activity limiting agents in the first reactor. The polypropylene homopolymer is introduced into the second reactor along with ethylene and optionally a selectivity control agent and/or an activity limiting agent. The selectivity control agent and the activity limiting agent may be the same as or different from the respective components used in the first reactor. This produces a propylene-ethylene copolymer in the second reactor.

In an embodiment, the olefin is propylene. The process includes forming a propylene-based polymer having a melt flow rate (MFR) from about 0.01 g/10 min to about 800 g/10 min, or from about 0.1 g/10 min to about 200 g/10 min, or from about 0.5 g/10 min to about 150 g/10 min. In a further embodiment, the propylene-based polymer is a polypropylene homopolymer.

In an embodiment, the olefin is propylene. The process includes forming a propylene-based polymer having a xylene solubles content from about 0.5% to about 10%, or from about 1% to about 8%, or from about 1% to about 4%. In a further embodiment, the propylene-based polymer is a polypropylene homopolymer.

In an embodiment, the olefin is propylene. The process includes forming a propylene-based polymer having a polydispersity index (PDI) from about 4 to about 15, or from about 4 to about 10, or from about 4 to about 8. In a further embodiment, the propylene-based polymer is a polypropylene homopolymer.

The present disclosure provides another process. In an embodiment, a polymerization process is provided and includes contacting propylene and ethylene and/or 1-butene with a catalyst composition under polymerization conditions. The catalyst composition may be any catalyst composition disclosed herein. The process includes forming a random propylene-based interpolymer having an MFR from about 0.01 g/10 min to about 200 g/10 min, or from about 0.1 g/10 min to about 100 g/10 min, or from about 0.5 g/10 min to about 70 g/10 min. The formant propylene-based interpolymer has a xylene solubles content from about 0.5% to about 40%, or from about 1% to about 30%, or from about 1% to about 20%.

The formant propylene-based interpolymer has a weight percent comonomer content relative to propylene of from about 0.001% to about 20%, or from about 0.01% to about 15%, or from about 0.1% to about 10%.

The catalyst composition and the catalyst system of the present disclosure are also well suited for producing impact resistant polymers that have rubber-like or elastomeric properties. These polymers are typically made in a two reactor system where it is desirable for the catalyst to maintain high activity levels. In one embodiment, for instance, the polymerization is performed in two reactors connected in series. A propylene homopolymer or a propylene copolymer can be formed in the first reactor in order to form an active propylene-based polymer. The active propylene-based polymer from the first polymerization reactor is then introduced into a second polymerization reactor and contacted, under second polymerization conditions, with at least one second monomer in the second reactor to form a propylene impact copolymer. In one embodiment, the process includes contacting the active propylene-based polymer with propylene and ethylene in the second polymerization reactor under polymerization conditions and forming a discontinuous phase of propylene/ethylene copolymer.

As described above, the first phase polymer can comprise a polypropylene homopolymer. In an alternative embodiment, however, the first phase polymer may comprise a random copolymer of polypropylene.

The random copolymer, for instance, can be a copolymer of propylene and an alpha-olefin, such as ethylene. The polypropylene random copolymer forms the matrix polymer in the polypropylene composition and can contain the alpha-olefin in an amount less than about 12% by weight, such as in an amount less than about 5% by weight, such as in an amount less than about 4% by weight, and generally in an amount greater than about 0.5% by weight, such as in an amount greater than about 1% by weight, such as in an amount greater than about 1.5% by weight, such as in an amount greater than about 2% by weight. The first phase polymer can have a xylene soluble content of generally less than about 12% by weight, such as in an amount less than about 10% by weight, such as in an amount less than about 8% by weight, such as in an amount less than about 6% by weight, such as in an amount less than about 4% by weight. The xylene soluble content is generally greater than about 0.5% by weight, such as greater than about 3% by weight.

The polypropylene random copolymer or polypropylene homopolymer that makes up the first phase polymer, in one embodiment, has a relatively high melt flow rate. For instance, the first phase polymer can have a melt flow rate of greater than about 5 g/10 mins, such as greater than about 10 g/10 mins, such as greater than about 15 g/10 mins, such as greater than about 20 g/10 mins, such as greater than about 25 g/10 mins. The melt flow rate of the first phase polymer is generally less than about 1000 g/10 mins, such as less than about 500 g/10 mins.

The second phase polymer is a propylene and alpha-olefin copolymer. The second phase polymer, however, has elastomeric or rubber-like properties. Thus, the second phase polymer can dramatically improve the impact strength resistance of the polymer.

The second phase polymer which forms a dispersed phase within the polymer composition contains the alpha-olefin or ethylene in an amount generally greater than about 10% by weight, such as in an amount greater than about 12% by weight, such as in an amount greater than about 14% by weight and generally less than about 35% by weight, such as less than about 20% by weight, such as in an amount less than about 17% by weight. The second phase polymer can have a weight average molecular weight of at least about 130,000, such as at least about 140,000, such as at least about 150,000 and generally less than about 500,000.

In an embodiment, the olefin-based polymer (i.e., propylene-based polymer) produced by any of the foregoing processes comprises a substituted phenylene as described above.

The present polymerization process may comprise two or more embodiments disclosed herein.

Not wishing to be bound by any particular theory, it is believed that the present catalyst compositions with substituted phenylene aromatic diester internal electron donor yield olefin-based polymers, high catalyst activity, and high stereoselectivity. Moreover, the present substituted phenylene aromatic diester advantageously provides the present procatalyst composition(s), catalyst composition(s), and olefin-based polymer(s) the property of being phthalate-free, or otherwise void or devoid of phthalate and/or derivatives thereof.

EXAMPLES

GENERAL PROCEDURES—Internal Electron Donor Synthesis

Internal electron donors used in the examples below were generally synthesized using the following methods.

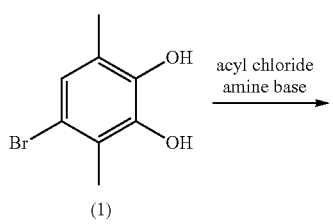

(1)

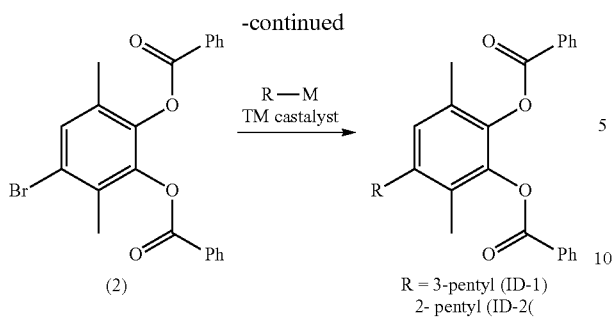

(2)　　　　R = 3-pentyl (ID-1)
　　　　　2-pentyl (ID-2)

Method A—Cross-Coupling Mediated Process Outline

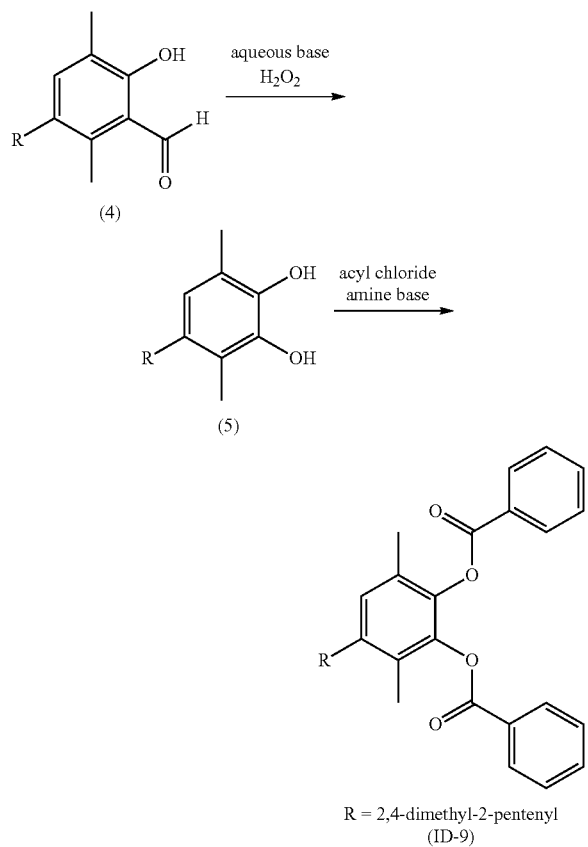

R = 2,4-dimethyl-2-pentenyl
(ID-9)

Method B—Transition-Metal Free Process Outline

The internal donors were produced by two different methods. Representative examples are given below.

Process Details: Method A

Synthesis of 4-bromo-3,6-dimethyl-1,2-phenylene dibenzoate (2)

An appropriate amine base is charged to a solution of 4-bromo-3,6-dimethyl-1,2-benzenediol (1) in organic solvent. The reactor is cooled contacted with an acyl chloride and allowed to warm to room temperature. Once complete, the reaction is quenched with water. The aqueous layer is separated off; and the organic fraction is neutralized. The solution is concentrated, generating an orange solid. The crude product is recrystallized in hydrocarbon solvent. Filtration gives 4-bromo-3,6-dimethyl-1,2-phenylene dibenzoate (2) as an off-white solid.

Synthesis of 4-(3-pentyl)-3,6-dimethyl-1,2-phenylene dibenzoate 4-bromo-3,6-dimethyl-1,2-phenylene dibenzoate (2) and a palladium catalyst are charged to an inert vessel. The solids are dissolved in an ethereal solvent, and an appropriate transmetallating partner is introduced to the reaction. The reaction is heated, and when complete, is quenched and diluted in an organic solvent. The organic fraction is washed with subsequent portions of water and washed. The product solution is then concentrated to a solid. The crude solid is recrystallized in an organic solvent. 4-(3-pentyl)-3,6-dimethyl-1,2-phenylene dibenzoate (ID-1) is isolated as a white solid.

Method B

Synthesis of 4-(3-(2,4-methyl-2-pentenyl))-3,6-dimethyl-2-hydroxy benzaldehyde (4)

4-(3-(2,4-methyl-2-pentenyl))-2,5-dimethyl phenol (3) and HMTA are dissolved in trifluoroacetic acid. The reaction is heated to completion, cooled, and then concentrated. Organic solvent and aqueous acid are added and heated for a period of time. Upon completion, the organic fraction is separated and concentrated to give 4-(3-(2,4-methyl-2-pentenyl))-3,6-dimethyl-2-hydroxy benzaldehyde (4).

Synthesis of 4-(3-(2,4-methyl-2-pentenyl))-3,6-dimethyl-1,2-benzene diol (5)

The previously prepared benzaldehyde (4) is dissolved a combination of ethereal solvent and water. The mixture is contacted with a basic aqueous solution and aqueous hydrogen peroxide. The reaction is heated until completion, cooled, and quenched with acidic media. The product layer is neutralized, dried, and concentrated to yield 4-(3-(2,4-methyl-2-pentenyl))-3,6-dimethyl-1,2-benzenediol (5).

Synthesis of 4-(3-(2,4-methyl-2-pentenyl))-3,6-dimethyl-1,2-phenylene dibenzoate (ID-9)

An appropriate amine base is charged to a solution of compound (5) in organic solvent. The reactor is cooled contacted with an acyl chloride and allowed to warm to room temperature. Once complete, the reaction is quenched with water. The aqueous layer is separated off; and the organic fraction is neutralized. The solution is concentrated, generating an orange solid. The crude product is recrystallized in hydrocarbon solvent. 4-(3-(2,4-methyl-2-pentenyl))-3,6-dimethyl-1,2-phenylene dibenzoate (ID-9) is isolated as an off-white solid.

GENERAL PROCEDURES— Polymerization Conditions

Homopolymerization at 70° C. A 2 L stainless steel autoclave equipped with overhead stirrer and thermostating jacket was purged with argon at 90° C. for one hour before cooling to 20° C. and exchanging the argon with propylene gas. A cocatalyst solution was prepared by mixing 2.3 mmol of triethylaluminum and 0.078 mmol of dicyclopentyldimethoxysilane in 15 ml of hexane. 6 ml of the cocatalyst solution was added to a charging tube A. The remainder was added to a charging tube B with approximately 3 mg of solid catalyst. Hydrogen (57 mmol) was added to the reactor and the contents of charging tube A was flushed into the reactor with 600 ml of propylene. Stirring was initiated and the contents of charging tube B were flushed into the reactor with 450 ml of propylene. The reactor was heated to 70° C. in 10 min and the polymerization was continued for 1 h. At the end of the polymerization the stirrer was turned off and non-reacted propylene was vented while cooling the reactor. The polymer was recovered and dried in a vacuum oven at 50° C. before weighing and analysis.

In cases where polymerizations were conducted in a 4 L autoclave the same general procedure was followed except charging tubes A & B were added with 1400 mL and 600 mL of propylene, respectively. Reagent amounts for 4 L polymerizations were: 2,000 ml of propylene, 252 mmmol hydrogen, 3.4 mmol of triethylaluminum, 0.131 mmol of dicyclopentyldimethoxysilane, and 8.0 mg of catalyst.

2-stage copolymerizations. The procedure described for homopolymerization at 70° C. was followed using a 4 L autoclave except after 45 min of polymerization the reactor pressure was reduced to 200 psig, hydrogen was added (100 mmol), and ethylene was added to 300 psig reactor pressure while raising the reactor temperature to 80° C. Polymerization was continued in gas phase at 80° C. and 300 psig for 45 min with continuous feeding of a 1/1 molar ethylene/propylene gas mixture. The results are collected in Table 4.

Low temperature polymerizations. The same general procedure described for homopolmyerization at 70° C. was followed using a 2 L autoclave except charging tubes A & B were added at the polymerization temperature and the polymerization was terminated after 30 min. Reagent amounts for low temperature polymerizations were: 1,050 ml propylene, 21 mmol hydrogen, 3.5 mmol triethlyalumnium, 0.175 mmol dicyclopentyldimethoxysilane, and 20 mg of catalyst. Results are collected in Table 5.

Melt flow rate was measured in accordance with ASTM D 1238-01 test method at 230° with a 2.16 kg weight for propylene-based polymers. Xylene Solubles (XS) was measured using a Crystex automated instrument by Polymer Char. The Crystex was calibrated with polypropylene homopolymer samples analyzed for XS by ASTM D 5492-10 test method.

A $MgCl_2$*EtOH adduct was prepared as described previously in U.S. Pat. No. 5,468,698. $MgCl_2$*EtOH adduct with average particle size of 58 micron was used for examples E-6 through E-13.

Internal donor structures for the examples are given in Table 1.

Examples

E-1 through E-5, E-14 and E-15. 4.0 g of a MagTi support (U.S. Pat. Nos. 5,124,298 and 5,962,361) is added to a 100 ml Schlenk flask and slurried with 20 ml monochlorobenzene (MCB). The slurry is transferred to a 1 L reactor under pure $N_2$ at room temperature. Another 20 ml of MCB is added to the support flask and used to rinse any remaining support into the reactor. Then 40 ml (70 g) of $TiCl_4$ that was either at room temperature or had been cooled to 10° C. is quickly added to the reactor. The slurry is heated to 25° C. and stirred at this temperature for 5 min.

Then 2.31 to 2.38 mmol of the donor dissolved in 6.5 to 7.0 ml of monochlorobenzene (MCB) is added to the reactor. The temperature is then ramped to 100° C. (in 40 min), and held there for 50 min. The stirring is stopped and the slurry is allowed to settle while maintaining the reactor at 100° C. The supernatant is decanted followed by the addition of 80 ml of a 50:50 volume mixture of $TiCl_4$ and MCB. The reactor is heated to 115° C. During the heat-up, 1.16 to 1.24 mmol of the donor dissolved in 3.5 ml of MCB is added. The reaction mixture is held at 115° C. for 25 min.

The stirring is stopped and the slurry is allowed to settle while maintaining the reactor at 115° C. The supernatant is decanted followed by the addition of 80 ml of a 50:50 volume mixture of $TiCl_4$ and MCB. The reactor is reheated to 115° C. and held at this temperature for 25 min. The stirring is stopped and the slurry is allowed to settle while maintaining the reactor at 115° C. The supernatant is decanted.

The reactor temperature is set to 25° C. Then 100 ml of heptane is added and stirred for 10 min before settling and decanting the wash. This is repeated 4 more times as the reactor cools with the last two washes being done with the reactor at 25° C. The wet solid is dried under vacuum for 2 h at 40° C. The catalyst composition and bulk polymerization testing data is shown in Table 2.

E-6:30 g of $MgCl_2$*EtOH precursor with EtOH/Mg mole ratio of 3.1 and 80 ml heptane were added to a 1 L jacketed glass reactor with overhead stirring and the mixture was cooled to −20° C. 520 g of $TiCl_4$ pre-cooled to −20° C. was added and stirring continued for 1 h. The reactor temperature was increased to 20° C. at a rate of 0.33° C./min. A solution of 2.25 g of ethylbenzoate in 10 ml of heptane was added by cannula. After completing the addition, the reactor temperature was increased to 85° C. at a rate of 0.54° C./min. During the temperature ramp a solution of 5.4 g of ID-1 in 45 ml of toluene was metered at a rate of 0.5 mL/min. After reaching 85° C., stirring was continued for 1 h before allowing catalyst solids to settle and decanting the supernatant. 520 g of pre-heated $TiCl_4$ was added, followed by a solution of 3.0 g of ID-1 in 23 ml of toluene, and the mixture was stirred for 1 h before repeating the settle and decant steps. The $TiCl_4$ treatment was repeated at 130° C. for 0.5 h. After settle and decant steps the reactor was cooled to 65° C. Catalyst solids were washed five times with heptane at 65° C., 300 ml each wash. The catalyst was then dried under vacuum at 40° C. for 4 h. Catalyst composition and bulk polymerization testing data are given in Table 3.

E-7:20 g of $MgCl_2$ precursor with EtOH/Mg mole ratio of 2.2 and 73 ml of heptane were added to a 1 L jacketed glass reactor with overhead stirring and the mixture was cooled to −20° C. 350 g of $TiCl_4$ pre-cooled to −20° C. was added and stirring continued for 1 h. The reactor temperature was increased to 20° C. at a rate of 0.33° C./min. A solution of 1.2 g of ethyl benzoate in 5 ml of heptane was added by cannual. After completing the addition, the reactor temperature was increased to 85° C. at a rate of 0.54° C./min. During the temperature ramp a solution of 1.8 g of ID-1 in 30 ml of toluene was metered at a rate of 0.4 mL/min. After reaching 85° C., stirring was continued for 1 h before allowing catalyst solids to settle and decanting the supernatant. 70 g of pre-heated $TiCl_4$ and 140 g of toluene were added, followed by 0.8 g of ID-1 in 10 ml of toluene, and the mixture was stirred at 105° C. for 1 h before repeating the settle and decant steps. The $TiCl_4$/toluene treatment was repeated at 120° C. for 1 h. After settle and decant the reactor was cooled to 65° C. Catalyst solids were washed five times with heptane at 65° C., 200 ml each wash. The catalyst was then dried under vacuum at 40° C. for 4 h. Catalyst composition and bulk polymerization testing data are listed in Table 3.

E-8 followed the same procedure as E-2 except 1.5 g of ethyl benzoate was charged, 1.8 g of ID-4 was used in the first charge, and 1.2 g of ID-4 was used in the second charge. E-9 followed the same procedure as E-3 using ID-6. $E_{10}$ followed the same procedure as E-1 using ID-7. E-11 followed the same procedure as E-1 using ID-8. E-12 followed the same procedure as E-3 using ID-7. The catalyst composition and bulk polymerization testing data are listed in Table 3.

E-13:20 g of $MgCl_2$ precursor with EtOH/Mg mole ratio of 3.1 and 70 ml of octane were added to a 1 L jacketed glass reactor with overhead stirring and the mixture was cooled to −20° C. 520 g of $TiCl_4$ pre-cooled to −20° C. was added and stirring continued for 1 h. The reactor temperature was increased to 20° C. at 0.44° C./min. A solution of 5.48 g of ethylbenzoate in 7 ml of octane was added by cannula. After completing the addition, the reactor temperature was increased to 105° C. at a rate of 0.95° C./min and stirring continued for 1.5 h before allowing catalyst solids to settle and decanting the supernatant. 520 g of pre-heated TiCl$_4$ was added, the reactor was heater to 115° C., a solution of 2.7 g of ID-1 in 10 ml of toluene was added, and the reactor was stirred for 0.5 h before repeating the settle and decant steps. TiCl$_4$ treatment was repeated at 125° C. for 0.5 h. After settle and decant steps the reactor was cooled to 65° C. Catalyst solids were washed five times with heptane at 65° C., 200 ml each wash. The catalyst was dried under vacuum at 40° C. for 4 h. Catalyst composition and bulk polymerization testing data are listed in Table 3.

E14: Prepared according to US2013/0261273 using internal donor ID-11

TABLE 1

Internal Donor Structures

| Donor Designation | Chemical Name | Structure |
|---|---|---|
| ID 1 | 4-(3-pentyl)-3,6-dimethyl-1,2-phenylene dibenzoate | 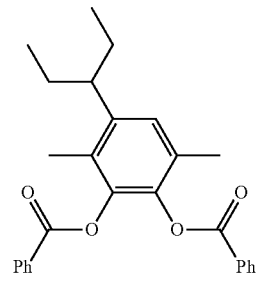 [SMILES: CCC(CC)c1cc(C)c(OC(=O)c2ccccc2)c(OC(=O)c2ccccc2)c1C] |
| ID 2 | 4-(2-pentyl)-3,6-dimethyl-1,2-phenylene dibenzoate | 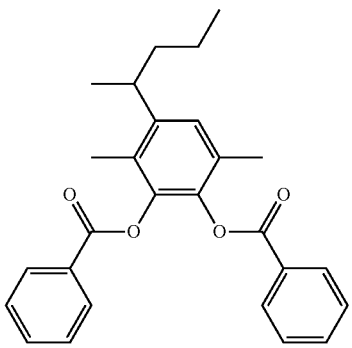 [SMILES: CCCC(C)c1cc(C)c(OC(=O)c2ccccc2)c(OC(=O)c2ccccc2)c1C] |
| ID 3 | 4-phenyl-3,6-dimethyl-1,2-phenylene dibenzoate | 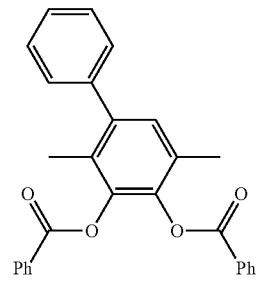 [SMILES: Cc1cc(-c2ccccc2)c(C)c(OC(=O)c2ccccc2)c1OC(=O)c1ccccc1] |

TABLE 1-continued

Internal Donor Structures

| Donor Designation | Chemical Name | Structure |
|---|---|---|
| ID 4 | 4-(2-tolyl)-3,6-dimethyl-1,2-phenylene dibenzoate | 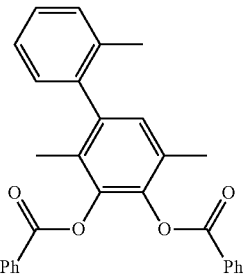 [SMILES: Cc1ccccc1-c1cc(C)c(OC(=O)c2ccccc2)c(OC(=O)c2ccccc2)c1C] |
| ID 5 | 4-(1-napthyl)-3,6-dimethyl-1,2-phenylene dibenzoate | 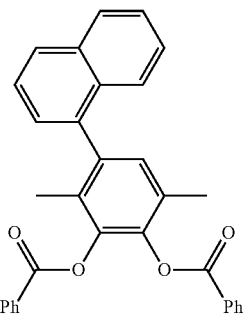 [SMILES: Cc1cc(-c2cccc3ccccc23)c(C)c(OC(=O)c2ccccc2)c1OC(=O)c1ccccc1] |
| ID 6 | 4-(cyclopentyl)-3,6-dimethyl-1,2-phenylene dibenzoate | 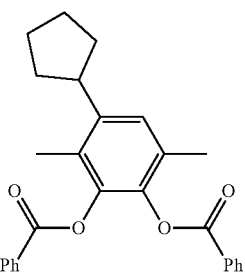 [SMILES: Cc1cc(C2CCCC2)c(C)c(OC(=O)c2ccccc2)c1OC(=O)c1ccccc1] |
| ID 7 | 4-(cycloheptyl)-3,6-dimethyl-1,2-phenylene dibenzoate | 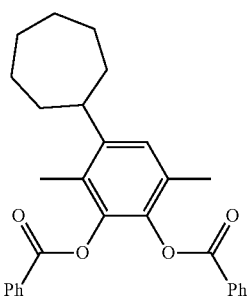 [SMILES: Cc1cc(C2CCCCCC2)c(C)c(OC(=O)c2ccccc2)c1OC(=O)c1ccccc1] |
| ID 8 | 4-(cyclo-octyl)-3,6-dimethyl-1,2-phenylene dibenzoate | 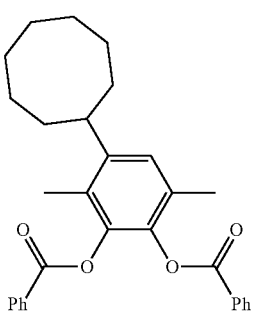 [SMILES: Cc1cc(C2CCCCCCC2)c(C)c(OC(=O)c2ccccc2)c1OC(=O)c1ccccc1] |

TABLE 1-continued

Internal Donor Structures

| Donor Designation | Chemical Name | Structure |
|---|---|---|
| ID 9 | 4-(3-(2,4-methyl-2-pentenyl))-3,6-dimethyl-1,2-phenylene dibenzoate | 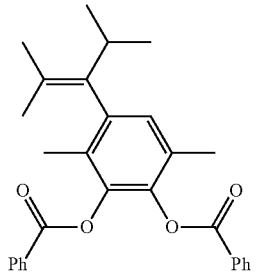 [SMILES: CC(C)=C(c1cc(C)c(OC(=O)c2ccccc2)c(OC(=O)c2ccccc2)c1C)C(C)C] |
| ID 10 | 4-(1-pentyl)-3,6-dimethyl-1,2-phenylene dibenzoate | 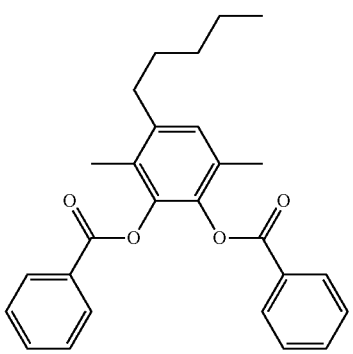 [SMILES: CCCCCc1cc(C)c(OC(=O)c2ccccc2)c(OC(=O)c2ccccc2)c1C] |
| ID 11 | 5-(t butyl) 3 methyl 1,2 phenylene dibenzoate | |

TABLE 2

Catalyst composition and homopolmyerization results

| | | Composition | | Polytest Results | | |
|---|---|---|---|---|---|---|
| Example | Donor | % Ti | % Donor | Activity, kg/g | MI dg/min | XS wt % |
| E-1 | ID 1 | 3.7 | 30.6 | 91[1] | 7 | 0.7 |
| E-2 | ID 2 | 3.7 | 23.7 | 98[2] | 9 | 2.1 |
| E-3 | ID 3 | 3.5 | 22.2 | 43[1] | 11 | 1.8 |
| E-4 | ID 4 | 3.7 | 26.0 | 50[1] | 6 | 1.2 |
| E-5 | ID 5 | 3.8 | 26.7 | 41[1] | 7 | 1.8 |
| E-14 | ID 9 | 3.6 | 20.7 | 71[1] | 11 | 1.5 |
| E-15 | ID 10 | 2.9 | 23.2 | 25[2] | 17 | 1.4 |

[1] 2 L reactor
[2] 4 L reactor

TABLE 3

Catalyst composition and homopolymerization results [a]

| Example | Donor | % Ti | % Donor | Activity, kg/g | MI dg/min | XS wt % |
|---|---|---|---|---|---|---|
| E-6 | ID-1 | 3.68 | 23.9 | 57.4 | 18.1 | 1.40 |
| E-7 | ID-1 | 3.22 | 17.7 | 60.9 | 13.9 | 1.52 |
| E-9 | ID-6 | 3.09 | 17.3 | 45.4 | 19.3 | 1.75 |
| E-10 | ID-7 | 3.07 | 21.3 | 69.4 | 11.1 | 1.77 |
| E-11 | ID-8 | 3.54 | 16.2 | 71.9 | 12.7 | 1.99 |

TABLE 3-continued

Catalyst composition and homopolymerization results [a]

| Example | Donor | % Ti | % Donor | Activity, kg/g | MI dg/min | XS wt % |
|---|---|---|---|---|---|---|
| E-12 | ID-7 | 2.95 | 20.2 | 61.5 | 18.7 | 1.69 |
| E-13 | ID-1 | 3.82 | 14.8 | 71.9 | 3.8 | 2.14 |

[a] 4L reactor.

TABLE 4

2-stage copolymerization results

| Catalyst | Activity, Kg/g | MI, dg/min | XS, wt % | Ethylene, wt % |
|---|---|---|---|---|
| E-12 (a) | 36.6 | 11.5 | 20.5 | 8.6 |
| E-13 | 63.9 | 11.8 | 28.9 | 7.1 |
| E 14 (b) | 45.7 | 6.7 | 8.9 | 1.6 | a) $C_2H_4/C_3H_6$ molar ratio of 1.5/1 was used
b) bulk propylene step = 30 min., $H_2$ charge in bulk step = 505 mmol

TABLE 5

Low temperature polymerization results

| Example | Pol-T, °C. | Yield, g | Mileage, g/g |
|---|---|---|---|
| E-6 | 15 | 15.3 | 757 |
| E-6 | 20 | 25.1 | 1224 |
| E-6 | 25 | 33.3 | 1649 |
| E 14 | 15 | 19.7 | 972 |
| E 14 | 20 | 30.6 | 1508 |
| E 14 | 25 | 41.9 | 2072 |

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention as further described in such appended claims.

What is claimed:

1. A catalyst composition for stereoselective polymerization of propylene comprising:
a combination of a magnesium moiety, a titanium moiety, and an internal electron donor, the internal electron donor comprising:

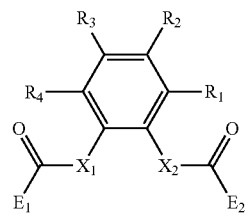

wherein:
$R_1$ and $R_4$ are each a hydrocarbyl group having from 1 to 20 carbon atoms;
$R_2$ is hydrogen;
$R_3$ is a substituted or unsubstituted hydrocarbyl group having from 5 to 15 carbon atoms, the hydrocarbyl group having a branched or linear structure or comprising a cycloalkyl group having from 7 to 15 carbon atoms;

$E_1$ and $E_2$ are the same or different and selected from the group consisting of an alkyl having 1 to 20 carbon atoms, a substituted alkyl having 1 to 20 carbon atoms, an aryl having 6 to 20 carbon atoms, a substituted aryl having 6 to 20 carbon atoms, and an inert functional group having 1 to 20 carbon atoms and optionally containing heteroatoms;

$X_1$ is $NR_5$ and $X_2$ is O, S, or $NR_5$, or $X_2$ is $NR_5$ and $X_1$ is O, S, or $NR_5$; and $R_5$ is a hydrocarbyl group having 1 to 20 carbon atoms or is hydrogen.

2. The catalyst composition of claim 1, wherein $R_3$ is a branched alkyl or alkenyl group.

3. The catalyst composition of claim 2, wherein the branched alkyl or alkenyl group contains from 5 to 10 carbon atoms.

4. The catalyst composition of claim 1, wherein $R_3$ is a 3-pentyl group, a 2-pentyl group, a cycloheptyl group, or a cyclooctyl group.

5. The catalyst composition of claim 1, wherein $R_1$ and $R_4$ are the same.

6. The catalyst composition of claim 1, wherein $R_1$ and $R_4$ are linear hydrocarbyl groups.

7. The catalyst composition of claim 1, wherein $R_1$ and $R_4$ comprise a C1 to C8 alkyl group, a C2 to C8 alkenyl group, or mixtures thereof.

8. The catalyst composition of claim 1, wherein the magnesium moiety comprises a magnesium halide.

9. The catalyst composition of claim 1, wherein $E_1$ and $E_2$ both comprise phenyl groups.

10. The catalyst composition of claim 1, further comprising a cocatalyst, optionally an activity limiting agent and optionally a selectivity control agent.

11. The catalyst composition of claim 10, wherein the cocatalyst comprises a hydrocarbon aluminum cocatalyst.

12. The catalyst composition of claim 10, wherein the selectivity control agent is present and comprises an alkoxysilane.

13. The catalyst composition of claim 10, wherein the selectivity control agent comprises dicyclopentyldimethoxysilane, di-tert-butyldimethoxysilane, methylcyclohexyldimethoxysilane, methylcyclohexyldiethoxysilane, ethylcyclohexyldimethoxysilane, diphenyldimethoxysilane, diisopropyldimethoxysilane, di-n-propyldimethoxysilane, diisobutyldimethoxysilane, diisobutyldiethoxysilane, isobutylisopropyldimethoxysilane, di-n-butyldimethoxysilane, cyclopentyltrimethoxysilane, isopropyltrimethoxysilane, n-propyltrimethoxysilane, n-propyltriethoxysilane, ethyltriethoxysilane, tetramethoxysilane, tetraethoxysilane, diethylaminotriethoxysilane, cyclopentylpyrrolidinodimethoxysilane, bis(pyrrolidino)dimethoxysilane, bis(perhydroisoquinolino)dimethoxysilane, dimethyldimethoxysilane or mixtures thereof.

14. The catalyst composition of claim 1, wherein the magnesium moiety comprises a spray crystallized magnesium halide compound comprising ethanol and magnesium chloride in a weight ratio of from about 1.5:1 to about 3.1:1.

15. A polymerization process comprising: polymerizing an olefin in the presence of a catalyst composition comprising the catalyst composition of claim 1.

16. The polymerization process of claim 15, wherein the olefin comprises propylene for forming a propylene homopolymer or comprises propylene and ethylene for forming a propylene and ethylene copolymer.

17. The polymerization process of claim 16, wherein the process produces a heterophasic polymer.

18. The polymerization process of claim 17, wherein the heterophasic polymer comprises a first polymer phase comprising a polypropylene homopolymer or a polypropylene random copolymer, the heterophasic polymer further comprising a second polymer phase combined with the first polymer phase, the second polymer phase comprising an elastomeric propylene ethylene copolymer.

19. The polymerization process of claim 18, wherein the first polymer phase is formed in a first reactor and the second polymer phase is formed in a second reactor, the catalyst composition remaining active in both the first reactor and the second reactor.

20. An olefin polymer containing the catalyst composition of claim 1.

21. The catalyst composition of claim 11, wherein the hydrocarbon aluminum cocatalyst comprises triethylaluminum.

* * * * *